(12) United States Patent
Sandoval et al.

(10) Patent No.: US 8,563,739 B2
(45) Date of Patent: Oct. 22, 2013

(54) RUTHENIUM COMPLEXES HAVING HYBRID AMINE LIGANDS, THEIR PREPARATION AND USE

(75) Inventors: Christian A Sandoval, Shanghai (CN); Yue-hui Li, Shanghai (CN)

(73) Assignees: Enantiotech Corporation Limited, Zhongshan (CN); Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 149 days.

(21) Appl. No.: 12/997,051

(22) PCT Filed: Jun. 12, 2009

(86) PCT No.: PCT/CN2009/072246
§ 371 (c)(1),
(2), (4) Date: Dec. 9, 2010

(87) PCT Pub. No.: WO2009/149670
PCT Pub. Date: Dec. 17, 2009

(65) Prior Publication Data
US 2011/0092712 A1     Apr. 21, 2011

(30) Foreign Application Priority Data
Jun. 13, 2008  (CN) .......................... 2008 1 0038929

(51) Int. Cl.
*C07F 15/00*     (2006.01)
(52) U.S. Cl.
USPC ........................................... 548/108; 548/109
(58) Field of Classification Search
USPC ................................................ 548/108, 109
See application file for complete search history.

(56) References Cited

PUBLICATIONS

DeVries, J. G. et al. (editors), *Handbook of Homogeneous Hydrogenation*, vol. 1, Wiley-Vch, (2007), contents only, 25 pages.
Knowles, W. S., *Asymmetric Hydrogenations—The Monsanto L-Dopa Process*, Asymmetric Catalysis on Industrial Scale: Challenges, Approaches and Solutions, Wiley-VCH (2004), pp. 23-38.
Ohkuma, T. et al., *Asymmetric Hydrogenation*, Catalytic Asymmetric Synthesis, Second Edition, Wiley-VCH (2000), pp. 1-7.

*Primary Examiner* — Joseph Kosack
(74) *Attorney, Agent, or Firm* — Alston & Bird LLP (57) ABSTRACT

The invention relates to a novel class of ruthenium complexes containing phosphine and hybrid amine ligands, their preparation and use as catalysts in the reduction of simple ketones to alcohols by molecular hydrogenation. The reactivity and enantioselectivity of such complexes in the asymmetric hydrogenation of simple ketones could be enhanced by the addition of some selective additives.

15 Claims, 1 Drawing Sheet

RUTHENIUM COMPLEXES HAVING HYBRID AMINE LIGANDS, THEIR PREPARATION AND USE

THE FIELD OF INVENTION

The invention relates to a novel class of ruthenium complexes containing phosphine and hybrid amine ligands, their preparation and use as catalysts in the reduction of simple ketones to alcohols by molecular hydrogenation. The reactivity and enantioselectivity of such complexes in the asymmetric hydrogenation of simple ketones can be enhanced by the addition of some additives.

BACKGROUND ART

Asymmetric catalytic hydrogenation is an area of intensive research within asymmetric synthesis. [Ohkuma, T.; Kitamura, M.; Noryori, R. (1999) Asymmetric Hydrogenation. In: *Catalytic Asymmetric Synthesis,* 2nd Ed. (Ed.: Ojima, I.). Wiley-VCH, New York, 2000*], [The Handbook of Homogeneous Hydrogenation* (Ed.: de Vries, J. G., Elsevier, C. J.). Wiley-VCH: Weinheim, 2007; Vol. 1-3.]. The efficiency and usefulness of the process is exemplified by several industrial applications so far developed. [*Asymmetric Catalysis on Industrial Scale* (Ed.: Blaser, H.-U.; Schmidt). Wiley-VCH, Weinheim, 2004].

Chiral alcohols are one of the important chiral compounds in the pharmaceutical, agrochemical and fine chemical industries, with asymmetric hydrogenation of ketone substrates the most effective way for the preparation of chiral alcohols. Noyori's research group have achieved the asymmetric hydrogenation of ketones by applying the concept of bifunctional catalysis in designing complexes of the type trans-RuCl$_2$(diphosphane)(1,2-diamine). In the presence of bases like t-BuOK or KOH, these type of complexes can catalyse the asymmetric hydrogentation of simple ketone substrates with excellent enantioselectivity and catalytic efficiency. [Noyori, R.; Takeshi, O.; Hirohito, O. Shohei, H.; Takao, I. *J. Am. Chem. Soc.* 1995, 117, 2675], [Noyori, R.; Ohkuma, T.; Douce, H.; Murata, K.; Yokozawa, T.; Kozawa, M.; Katayama, E.; England, A. F.; Ikariya, T., *Angew. Chem. Int. Ed.* 1998, 37, 1703]. With various combinations of new design bidentate ligands, such complexes have been successfully used in the asymmetric hydrogenation of a wide range of ketone substrates. [Jing, W.; Hua, C.; Waihim, K.; Rongwei, G.; Zhongyuan, Z.; Chihung, Y.; Chan, A. S. C., *J. Chem. Soc.* 2002, 67, 7908], [Jing, W.; Jian, X.; Rongwei, G.; Chihung, Y.; Chan, S. C., *Chem. Eur. J.* 2003, 9, 2963], [Jian, H. X.; Xin, L. W.; Fu, Y.; Shuo, F. Z.; Bao, M. F.; Hai, F. D.; Zhou, Q. L. *J. Am. Chem. Soc.* 2003. 125, 4404], [Mark, J.; William, H.; Daniela, H.; Christophe, M.; Antonio, Z. G. *Org. Lett.* 2000, 26, 4173].

Recently Noyori's group has devised a new catalyst, RuCl$_2$(phosphane)(α-picolylamine). By changing the diamine ligand to a hybrid amine ligand having structural motif of NH$_2$—N(sp$^2$), they can reduce ketones having a sterically bulky tert-butyl group on the α-position to the corresponding chiral secondary alcohol. This type of catalyst is by far the most active hydrogenation catalyst toward these particularly difficult ketone substrates. It is worth noting that the chiral tert-butyl alcohols are important for the preparation of some useful chiral surfactants. The common Ru complex of diphosphine-diamine type can only result in low conversion and low enantioselectivity (<20% e.e and conversion) in the reduction of these particular class of ketone substrates. [Ohkuma, T.; Sandoval, C. A.; Srinivasan, R.; Lin, Q.; Wei, Y.; Muñiz, K.; Noyori R. *J. Am. Chem. Soc.* 2005, 127, 8288.].

The major drawback for all aforementioned NH$_2$-ligand containing catalyst systems is the necessary use of protonic solvents and basic conditions during the hydrogenation reaction. The employment of protonic solvents may limit the scope of ketone substrates being applied in this catalytic hydrogenation methodology due to solubility issues, and also unfavourably interact with additional functionalities when more elaborate substrates are involved. Furthermore the difficulties on accessing a wide range of vicinal chiral diamine ligands are another limitation for the preparation of such catalyst systems. After our systematic study on the mechanism of this ketone reduction using RuCl$_2$(phosphane)(α-picolylamine or 1,2-diamine) as hydrogenation catalyst, we are able to design a new class of ruthenium complexes having a new hybrid NH$_2$—N(sp$^2$) structural motif as bidentate amine ligand that can catalyse the hydrogenation of simple aryl ketone in both aprotonic (eg. toluene, THF) and protonic solvents, in contrast to current catalyst system that only work in protonic solvents.

SUMMARY OF THE INVENTION

One of the objects for this invention is to provide a new class of ruthenium complexes, which contain both phosphine and hybrid amine ligands featuring the NH$_2$—N(sp$^2$) structural motif.

Another aspect of the invention is to provide a preparation process of the aforementioned ruthenium complexes by using the readily available hybrid chiral amine ligands.

A further aspect of the invention is the use of the said complexes in the catalytic asymmetric hydrogenation of simple ketone substrates, particular the catalytic asymmetric hydrogenation of simple ketones with aryl or unsaturated alkyl group on α-position, diaryl ketones and their analogues, ketones having bulky alkyl group on α-position, ketones having heteroaromatic group on α-position, α-phenyl-β-N,N-dimethylalkyl ketones and their analogues, and other simple aryl-alkyl ketone substrates.

A further aspect of the invention is the use of the said ruthenium complexes in the catalytic hydrogenation of simple ketones in both protonic and aprotonic solvents.

A further aspect of the invention is the use of additives with the said ruthenium complexes in the catalytic hydrogenation of ketones. The use of some additives can improve the rate of the hydrogenation or the enantioselectivity in the reaction. The additives can be selected from the group of monodentate tertiary phosphines or monodentate tertiary amines, such as triphenylphosphine, tri(4-methoxyphenyl)phosphine, tri(3,5-dimethylphenyl)phosphine, tri(3-methylphenyl)phosphine, diphenyl-2-naphthyl phosphine, triethylamine.

DETAILED DESCRIPTION OF THE INVENTION

The invention therefore provides the ruthenium complexes with a general formula (I) [RuLmL'XY] in which, X and Y can be equal or different, X can be a halogen (Cl, Br, I) or hydrogen, Y can be a halogen (Cl, Br, I) or BH$_4$ correspondingly.

L is the ligand selected from the following groups:

a) monophosphine having general formula $PR^1R^2R^3$, wherein $R^1, R^2, R^3$ can be equal or different and be aliphatic alkyl groups or aromatic groups having from 1 to 6 carbon atoms;

b) bidentate phosphine with general formula $R^5R^6P—R^4—^7R^8$, wherein $R^4$ represented an organic hydrocarbon backbone that can be chiral or achiral; $R^5, R^6, R^7$ and $R^8$ can be equal or different, and be aliphatic alkyl group or aromatic groups having from 1 to 10 carbons;

with m become 2 in the case of equal monodentate phosphine ligands selected from a), and m become 1 in case of a bisphosphine selected from b).

L' is the bidentate hybrid amine ligand selected from the following groups (II to V):

II

III

IV

V wherein $R^9$ can independently be hydrogen, alkyl groups having 1 to 6 carbon atoms, when $R^9$ is not a hydrogen, the aforementioned hybrid amine ligands (II to V) are chiral ligands having either R or S configuration; the alkyl group for R9 is selected from the groups comprising methyl, ethyl, propyl, isopropyl, butyl, isobutyl, tertiary-butyl, isopentyl, cyclopentyl, isohexyl, cyclohexyl, phenyl.

$R^{10}, R^{11}, R^{12}$ can be independently hydrogen or alkyl groups, aryl groups, arylalkyl groups, each having up to 12 carbon atoms; the alkyl groups can be selected from the group comprising methyl, ethyl, propyl, butyl, isobutyl, tertiary-butyl, pentyl, hexyl, isopentyl, cyclopentyl, cyclohexyl; the aryl groups can be selected from phenyl, substituted phenyls, the arylalkyl group can be selected from benzyl, alkyl-substituted benzyl.

A can be independently alkyl, alkoxy, aryl, each having from 1 to 8 carbon atoms; A can also be independently hydrogen, halogen, nitro, amino, sulfonic acid; n is an integer from 1 to 4 equal to the number of unsubstituted aromatic ring carbons; the alkyl group for A is selected from the groups comprising methyl, ethyl, propyl, isopropyl, butyl, isobutyl, tertiary-butyl, isopentyl, cyclopentyl, cyclohexyl, fluoromethyl, trifluoromethyl; alkoxy group for A can be methoxy, ethoxy, tertiary-butoxy; aryl group for A can be phenyl, substituted phenyl, benzyl and substituted benzyl.

The aforementioned hybrid amine ligands can be conveniently prepared with methods known in the art of organic synthesis.

The said Ru complexes represented by the general formula (I) can be further illustrated by the following general structures as:

trans cis

The complexes can be trans or cis configuration, in which P represents the phosphine ligands that coordinate to the ruthenium as defined above (vide supra); the phosphine ligands used in this invention include but not limit to the following: triphenyl phosphine, BINAP and its analogue bisphosphine having binaphthyl or substituted binaphthyl backbone, BIPHEP and its analogue bisphosphines having biphenyl or substituted biphenyl backbone, JOSIPHOS and similar bisphosphine with a ferrocene or substituted ferrocene backbone, DIOP, chiraphos, skewphos, norphos, segphos, phanephos etc.

The structure represents the bidentate hybrid amine ligands that can be selected from the groups represented by formula II, III, IV and V as above; X can be hydrogen, halogen, Y can be hydrogen, halogen or $BH_4$.

The complexes representing by formula I can be prepared by ligand replacement methods known in the art. Usually the said complexes can be prepared by mixing the ruthenium compounds, the hybrid amine ligands, bidentate or monodentate phosphine ligands in organic solvents under 20~120° C. for 0.5~20 hours. The reaction molar ratio for the ruthenium compound, amine ligand and phosphine ligand can be 1:1~3:1~5, the phosphine ligand is represented by structure P, bidentate amine ligand is represented by structure formula:

in which P and $R^9$ are denoted as above. When monodentate phosphines are employed, the molar ratio for rethenium compound, amine ligand and monodentate phosphine ligand is 1:1~3:3~5, the recommended ratio is 1:2:4; when bidentate phosphines are employed, the molar ratio become 1:1~3:1~3, the recommended ratio is 1:2:2. The ruthenium metal compounds can be the halogenide of Ru complexes or their derivatives, such as $[RuX_2(C_6H_6)_2]_2$, $RuX2(PPh_3)_3$, $RuX_3$, wherein X is the halogen (Cl, Br, I).

Their preparation can be illustrated by the following reaction scheme using the ruthenium complexes as example:

When the Y is $BH_4$ in the complex of the said general formula, its preparation can be described here:

In the reaction scheme, P represents the phosphine ligand as defined above.

The solvents used in all above synthetic schemes can be organic solvents selected from benzene, dimethyl benzene, trimethyl benzene, acetonitrile, diethyl ether, THF, dimethyl ethylene ether, chloroform, dichloromethane, methanol, ethanol, isopropanol, N—N-dimethylformamide, N—N-dimethylacetamide, DMSO, N-methylpyrrole etc.

The preparation of the said Ru complexes and chiral amine ligands of this invention is simple to operate. The said Ru complexes are useful as catalyst in the hydrogenation of simple ketones, particularly the asymmetric hydrogenation of ketones having aryl or unsaturated alkyl group on a-position, ketones having bulky alkyl group on a-position, diaryl ketones and its derivatives, ketones having heteroaromatic group on α-position, β-N—N-dimethylamino-α-phenyl ketones and its derivatives, and other simple alkyl-aryl ketones. When the said Ru complexes are being used in the hydrogenation of simple ketones, the said Ru complexes can be prepared in situ for the hydrogenation reaction.

The catalytic reactivity of the said ruthenium complexes can be enhanced with the use of some additives, the additives can be selected from the groups of monodentate tertiary phosphines or monodentate tertiary amines, such as triphenylphosphines, tri(4-methylphenyl)phosphines, tri(4-methoxyphenyl)phosphine, tri(3,5-dimethylphenyl)phosphine, triethylamine etc. It is also found that such type of additives can also increase the enantioselectivity of the said ruthenium complexes in the asymmetric hydrogenation of simple ketones when the said ruthenium complexes are chiral. The molar ratio for the additives against the ruthenium metal is in the range of 3~1:1 (additive:Ru).

The invention can be illustrated by the following examples, and these examples are not intended to limit the scope of the invention.

A. Synthesis of Ruthenium Complexes

Synthesis of Complexes using $C_2$ symmetric bis-P ligands (DIOP, BINAP, Cl-MeO-BIPHEP, SEGPHOS, PhanePHOS, DIPAMP, DuPHOS, BDPP, CHIRAPHOS, PPM, PYRPHOS) uses the compound [RuCl$_2$(benzene)], $RuCl_2(PPh_3)_3$ and trans-RuCl$_2$(NBD)(py)$_2$ as the starting material, while the complexes were prepared in accordance with the procedure published in the literature (Noyori, R.; Takeshi, O.; Hirohito, O. Shohei, H.; Takao, I. *J. Am. Chem. Soc.* 1995, 117, 2675; Akotsi, O. M.; Meters, K.; Reid, R. D.; McDonald, R.; Bergens, S. H. *Chirality* 2000, 12, 514-522; BINAP=2,2'-bis(diphenylphosphino)-1,1'-binaphthyl, DIOP=4,5-Bis(diphenylphosphinomethyl)-2,2-dimethyl-1,3-dioxolane, Cl-MeO-BIPHEP=5,5'-Dichloro-6,6'-dimethoxy-2,2'-bis(diphenylphosphino)-1,1'-biphenyl, SEGPHOS=5,5'-Bis(diphenylphosphino)-4,4'-bi-1,3-benzodioxole, PhanePHOS=4,12-Bis(diphenylphosphino)-[2.2]-paracyclophane, DIPAMP=1,2-Bis[(2-methoxyphenyl)(phenyl)phosphino]

ethane, Me-DuPHOS=1,2-Bis((2S,5S)-2,5-dimethylphospholano)benzene, BDPP=2,4-Bis(diphenylphosphino)pentane, CHIRAPHOS=Bis(diphenylphosphino)butane, PYRPHOS=3,4-bis(diphenylphosphino)-Pyrrolidine, PPM=4-(diphenylphosphino)-2-[(diphenylphosphino)methyl]-Pyrrolidine. Synthesis of Complexes using $C_1$ symmetric bis-P ligand (JosiPHOS, WalPHOS, MandyPHOS) uses the compound $RuCl_2(PPh_3)_3$ as the starting material which can be obtained easily from hydrated $RuCl_3$ and $PPh_3$ (Steohenson, T. A.; Wilkinson, G. *J. Inorg. Nucl. Chem.* 1966, 28, 945-956; Josiphos=1-[Diarylphosphano]-2-[1-(dicyclohexylphosphano)ethyl]ferrocene.), while the complexes and $RuCl_2[(R,S)\text{-Josiphos}](PPh_3)$ were prepared in accordance with the procedure published in the literature (Baratta, W.; Ballico, M.; Chelucci, G.; Siega, K.; Rigo, P. *Angew. Chem. Int. Ed.* 2008, 47, 4362-4365). The monochloride complex (11) was prepared from (10) by reacting with $Et_3N$. The pre-catalysts used for in situ hydrogenation were $[RuCl_2BINAP(pyridine)_2$, $RuCl_2DIOP(pyridine)_2$, $RuCl_2(Josiphos)(pyridine)_2]$. As non-limiting examples of the present invention the synthesis and the characteristics of the complexes (8-25) are described in detail. All the syntheses were carried out under argon atmosphere, using freshly distilled solvents.

Example 1

Synthesis of $C_1$ symmetric complex
$RuCl_2[(R,S)\text{-Josiphos}][(S)\text{-Me-bimaH}]$ [(RS,S)-8]

$RuCl_2(PPh_3)_3$ (250 mg, 0.26 mmol) or trans-$RuCl_2(NBD)(py)_2$ (110 mg, 0.26 mmol) and (R,S)-Josiphos (165 mg, 0.26 mmol) were dissolved in $CH_2Cl_2$ (5 mL) and placed in a 20-mL Schlenk under an Ar atmosphere. Ar was bubbled through the solution for 5 min and the solution was stirred for 12 h. Following solvent removal under vacuum, (S)-Me-BimaH [(S)-Me-7] (42 mg, 0.26 mmol) was added together with degassed toluene (2 mL). The suspension was then heated at 100° C. for 4 h. Reduction of the volume to ca. 0.5 mL and addition of ether (5 mL) yielded a yellow precipitate. The supernatant was removed by filtration and the resulting powder was dried in vacuo to give 8 as a mixture of isomers.

Yield 190 mg (79%); MS (MALDI) m/z: 892 [M-Cl]$^+$; Elemental analysis, calcd. (%) for $C_{45}H_{55}Cl_2N_3P_2FeRu \cdot H_2O$: C, 57.15; H, 6.07; N, 4.44. Found: C, 58.01; H, 6.06; N, 4.34. Major isomer (ca 61%): $^1H$ NMR (300 MHz, DMSO-$d_6$, 21° C.): δ 14.26 (br, 1H, imidazole-NH), 7.88-7.28 (m, 14H, aromatic protons), 5.03 (m, 1H, PCH), 4.75-4.68 (m, 2H), 3.92-3.51 (m, 7H, $C_5H_5$ and CHMe), 2.31-0.86 (m, 30H, $C_6H_{11}$, $NH_2$ and $CH_3$); $^{13}C$ NMR (100 MHz, DMSO-$d_6$, 21° C.): d 157.3 (s, NCCMe), 143.5-123.3 (m, aromatic carbons), 111.7 (d, J(C,P)=7.5 Hz, $FeC_5H_3$), 96.5 (d, J(C,P)=3.6 Hz, $FeC_5H_3$), 72.5 (d, J(C,P)=3.1 Hz, $FeC_5H_3$), 71.0 (s, $FeC_5H_3$), 70.3 (s, $FeC_5H_5$), 68.8 (d, J(C,P)=4.8 Hz, $FeC_5H_3$), 51.2 (s, NCMe), 36.0 (d, J(C,P)=21.1 Hz, PCMe), 35.2-25.0 (m, $CH_2$ of Cy), 21.0 (s, NCMe), 14.9 (d, J(C,P)=7.2 Hz, PCMe); $^{31}P$ NMR (121 MHz, DMSO-$d_6$): δ 57.8 (d, $^2J(P,P)$=41.1 Hz), 41.8 (d, $^2J(P,P)$=41.1 Hz);

Example 2

Synthesis of the complex trans-$RuCl_2$-[(S,S)-DIOP][(S)-Me-bimaH] [(SS,S)-9]

The complex $[RuCl_2(benzene)]_2$ (4.8 mg, 0.019 mmol) and (S,S)-DIOP (9.7 mg, 0.019 mmol) were suspended in 3 ml of degassed DMF. After stirring for 1 hour at 100° C., the solvent was removed under high vacuum at 50° C. for 2 hours. After (S)-Me-bimaH (3.1 mg, 0.019 mmol) and 3 ml of degassed $CH_2Cl_2$ were added following 5-hours stirring at room temperature, the volume of the solution was reduced to about 0.5 ml and the complex was precipitated by adding 6 ml of hexane. The solid obtained was filtered off, washed twice with 3 ml of ethyl ether and dried under vacuum.

Yield 12.3 mg (76%). $^{31}P$ {$^1H$} NMR (162 MHz, CDCl$_3$, 20° C.) δ 40.7 (d, $^2J(P,P)$=42.6 Hz), 28.6 (d, $^2J(P,P)$=42.6 Hz); MS (MALDI) m/z: 796.0 [M-Cl]$^+$.

Example 3

Synthesis of the complex cis-$RuCl_2$[(S,S)-DIOP][(S)-Me-bimaH] [(SS,S)-10]

-continued (SS,S)-10

The complex (9) (20 mg, 0.024 mmol) was suspended in 3 ml of degassed toluene. After stirring for 2 hour at 110° C., the volume of the solution was reduced to about 0.5 ml and the complex was precipitated by adding 6 ml of hexane. The solid obtained was filtered off, washed twice with 3 ml of ethyl ether and dried under vacuum.

Yield 17.3 mg (86%). $^{31}$P {$^1$H} NMR (162 MHz, CDCl$_3$, 20° C.) δ 48.8 (d, $^2$J(P,P)=37.9 Hz), 29.8 (d, $^2$J(P,P)=37.3 Hz).

Example 4

Synthesis of the monochloride complex RuCl[(S,S)-DIOP][(S)-Me-bima] [(SS,S)-11]

The complex (10) (20 mg, 0.024 mmol) and Et$_3$N (5.2 μl, 0.036 mmol) was suspended in 3 ml of degassed toluene. After stirring for 2 hour at 60° C., the solvent was removed under high vacuum. After dissolving in 5 ml of CH$_2$Cl$_2$ and filtration, the volume was reduced to about 0.5 ml and the complex was precipitated by adding 6 ml of hexane. The solid obtained was filtered off, washed twice with 3 ml of ethyl ether and dried under vacuum.

Yield 18.2 mg (94%). $^{31}$P {$^1$H} NMR (162 MHz, CDCl$_3$, 20° C.) δ 39.6 (d, $^2$J(P,P)=39.0 Hz), 23.8 (d, $^2$J(P,P)=39.0 Hz).

Example 5

Synthesis of the complex trans-RuCl$_2$[(S)-BINAP][(S)-Me-bimaH] [(S,S)-12]

(SS,S)-12

The complex [RuCl$_2$(benzene)]$_2$ (6.6 mg, 0.013 mmol) and (S)-BINAP (16.4 mg, 0.026 mmol) were suspended in 3 ml of degassed DMF. After stirring for 1 hour at 100° C., the solvent was removed under high vacuum at 50° C. for 2 hours. After (S)-Me-bimaH (4.3 mg, 0.026 mmol) and 3 ml of degassed CH$_2$Cl$_2$ were added following 5-hours stirring at room temperature, the volume of the solution was reduced to about 0.5 ml and the complex was precipitated by adding 5 ml of hexane. The solid was obtained by filtration following with dryness under vacuum.

Yield 19 mg (71%). $^{31}$P {$^1$H} NMR (121 MHz, CDCl$_3$, 20° C.) δ (ppm) 49.58 (d, J=38.7 Hz), 47.32 (d, J=38.7 Hz); MS (MALDI) m/z: 884 [M-71]$^+$.

Example 6

Synthesis of the complex trans-RuCl$_2$[(S)-PhanePHOS][(S)-Me-bimaH] [(S,S)-13]

The complex [RuCl$_2$(benzene)]$_2$ (5.8 mg, 0.023 mmol) and (S)-PhanePHOS (13.5 mg, 0.023 mmol) were suspended in 3 ml of degassed DMF. After stirring for 1 hour at 100° C., the solvent was removed under high vacuum at 50° C. for 2 hours. After (S)-Me-bimaH (3.7 mg, 0.023 mmol) and 3 ml of degassed CH$_2$Cl$_2$ were added following 5-hours stirring at room temperature, the volume of the solution was reduced to about 0.5 ml and the complex was precipitated by adding 6 ml of hexane. The solid obtained was filtered off, washed twice with 3 ml of ethyl ether and dried under vacuum.

Yield 17.6 mg (84%). $^{31}$P {$^1$H} NMR (162 MHz, CDCl$_3$, 20° C.) δ 47.26 (d, J=31.0 Hz), 42.71 (d, J=31.0 Hz).

Example 7

Synthesis of the complex trans-RuCl$_2$[(S)-SEGPHOS][(S)-Me-bimaff] [(S,S)-14]

The complex [RuCl$_2$(benzene)]$_2$ (5.8 mg, 0.011 mmol) and (S)-SEGPHOS (14.1 mg, 0.023 mmol) were suspended in 3 ml of degassed DMF. After stirring for 1 hour at 100° C., the solvent was removed under high vacuum at 50° C. for 2 hours. After (S)-Me-bimaH (3.7 mg, 0.023 mmol) and 3 ml of degassed CH$_2$Cl$_2$ were added following 5-hours stirring at room temperature, the volume of the solution was reduced to about 0.5 ml and the complex was precipitated by adding 6 ml of hexane. The solid obtained was filtered off, washed twice with 3 ml of ethyl ether and dried under vacuum.

Yield 15.4 mg (71%). $^{31}$P {$^1$H} NMR (162 MHz, CDCl$_3$, 20° C.) δ 46.90 (d, J=36.3 Hz), 32.75 (d, J=36.3 Hz).

Example 8

Synthesis of the complex trans-RuCl$_2$[(S)—Cl-MeO-BIPHEP] [(S)-Me-bimaH] [(S,S)-15]

The complex [RuCl$_2$(benzene)]$_2$ (3.3 mg, 7 μmol) and (S)—Cl-MeO-BIPHEP (8.5 mg, 0.013 mmol) were suspended in 3 ml of degassed DMF. After stirring for 1 hour at 100° C., the solvent was removed under high vacuum at 50° C. for 2 hours. After (S)-Me-bimaH (2.1 mg, 0.013 mmol) and 3 ml of degassed CH$_2$Cl$_2$ were added following 5-hours stirring at room temperature, the volume of the solution was reduced to about 0.5 ml and the complex was precipitated by adding 6 ml of hexane. The solid obtained was filtered off, washed twice with 3 ml of ethyl ether and dried under vacuum.

Yield 11.7 mg (91%). $^{31}$P {$^1$H} NMR (162 MHz, CDCl$_3$, 20° C.) δ 48.42 (d, J=29.7 Hz), 46.18 (d, J=29.7 Hz).

Example 9

Synthesis of the mono-phosphine complex RuCl$_2$(PPh$_3$)$_2$[(S)-Me-bimaH] [(S,S)-16]

The complex RuCl$_2$(PPh$_3$)$_3$ (153 mg, 0.16 mmol) was suspended in 3 ml of degassed toluene. After stirring for 1 hour at room temperature, (S)-Me-bimaH (26 mg, 0.16 mmol) was added following with refluxing for 2 hour. The solvent was then reduced to about 0.5 ml and the complex was precipitated by adding 5 ml of hexane. The solid was obtained by filtration followed by removal of volatiles under vacuum.

Yield 101 mg (71%). $^{31}$P {$^{1}$H} NMR (121 MHz, CDCl$_3$, 20° C.) δ 43.72, 45.34 ppm.

Example 10

Synthesis of the tetrazole complex RuCl$_2$(PPh$_3$)$_2$ [(S)-Me-temaH] [(S,S)-17]

Using the same method as described in example 9.

Yield 74%. $^{31}$P {$^{1}$H} NMR (121 MHz, CDCl$_3$, 20° C.) δ 42.80, 44.62 ppm.

Example 11

Synthesis of the complex RuCl$_2$[(S)-BINAP][(S)-Me-temaH] [(S,S)-18]

The complex [RuCl$_2$(benzene)]$_2$ (6.6 mg, 0.013 mmol) and (S)-BINAP (16.4 mg, 0.026 mmol) were suspended in 3 ml of degassed DMF. After stirring for 1 hour at 100° C., the solvent was removed under high vacuum at 50° C. for 2 hours. After (S)-Me-temaH (4.3 mg, 0.026 mmol) and 3 ml of degassed CH$_2$Cl$_2$ were added following 5-hours stirring at room temperature, the volume of the solution was reduced to about 0.5 ml and the complex was precipitated by adding 5 ml of hexane. The solid was obtained by filtration following with dryness under vacuum.

Yield 19 mg (86%). $^{31}$P {$^{1}$H} NMR (121 MHz, CDCl$_3$, 20° C.) δ (ppm) 47.61, 49.15.

Example 12

Synthesis of the complex RuCl$_2$[(S)-BINAP][trimaH] [(S)-19]

The complex [RuCl$_2$(benzene)]$_2$ (9.3 mg, 0.018 mmol) and (S)-BINAP (23.0 mg, 0.036 mmol) were suspended in 3 ml of degassed DMF. After stirring for 1 hour at 100° C., the solvent was removed under high vacuum at 50° C. for 2 hours. Following addition of trimaH (4.7 mg, 0.036 mmol) and 3 ml of degassed CH$_2$Cl$_2$, the solution was stirred for 5-hours at room temperature. The volume of the solution was reduced to ca 0.5 ml and the complex was precipitated by adding 5 ml of hexane. The final solid was obtained by filtration followed by removal of volatiles under vacuum.

Yield 23.6 mg (71%). $^{31}$P {$^{1}$H} NMR (121 MHz, CDCl$_3$, 20° C.) δ (ppm) 47.5, 49.2.

Example 13

Synthesis of the complex RuCl$_2$[(S)-BINAP][dimaH] [(S)-20]

The complex [RuCl$_2$(benzene)]$_2$ (7.9 mg, 0.016 mmol) and (S)-BINAP (19.7 mg, 0.032 mmol) were suspended in 3 ml of degassed DMF. After stirring for 1 hour at 100° C., the solvent was removed under high vacuum at 50° C. for 2 hours. Following addition of dimaH (4.2 mg, 0.032 mmol) and 3 ml of degassed CH$_2$Cl$_2$, the solution was stirred for 5-hours at room temperature. The volume of the solution was reduced to ca 0.5 ml and the complex was precipitated by adding 5 ml of hexane. The final solid was obtained by filtration followed by removal of volatiles under vacuum.

Yield 19.2 mg (65%). $^{31}$P {$^{1}$H} NMR (121 MHz, CDCl$_3$, 20° C.) δ (ppm) 46.2, 48.6.

Example 14

Synthesis of complex RuCl$_2$[(R,S)-Josiphos](bimaH)[(R,S)-21]

Using the same method as example 1.
Yield 71%. $^{31}$P {$^{1}$H} NMR (121 MHz, CDCl$_3$, 20° C.) δ (ppm) 63.51, 41.81.

Example 15

Synthesis of RuCl$_2$[(R,S)-Josiphos][(S)-iPr-bimaH] [(RS,S)-22]

Using the same method as example 1.
Yield 76%. $^{31}$P {$^1$H} NMR (121 MHz, CDCl$_3$, 20° C.) δ (ppm) 63.67, 40.04.

Example 16

Synthesis of the complex trans-RuCl$_2$[(S,S)-DIOP] [(S)-iPr-bimaH] [(SS,S)-23]

Using the same method as example 2.
Yield 87%. $^{31}$P {$^1$H} NMR (162 MHz, CDCl$_3$, 20° C.) δ 39.8 (d, J=42.1 Hz), 26.3 (d, J=42.1 Hz).

Example 17

Synthesis of the complex trans-RuCl$_2$[(S,S)-DIOP] [(S)-tBu-bimaH] [(SS,S)-24]

Using the same method as example 2.
Yield 82%. $^{31}$P {$^1$H} NMR (162 MHz, CDCl$_3$, 20° C.) δ 40.5 (d, J=41.8 Hz), 27.9 (d, J=41.8 Hz).

Example 18

Synthesis of the complex trans-RuCl$_2$[(S,S)-DIOP] [(S)-Bn-bimaH] [(SS,S)-25]

Using the same method as example 2.
Yield 88%. $^{31}$P {$^1$H} NMR (162 MHz, CDCl$_3$, 20° C.) δ 39.9 (d, J=43.2 Hz), 28.6 (d, J=43.2 Hz).

B. Catalytic Tests in Asymmetric Hydrogenation

Example 19

A typical in situ hydrogenation using R-bimaH (7)

Accurately weighed amounts of RuCl$_2$[(R,S)-Josiphos] (PPh$_3$) (1.1 mg, 0.33 mM) or trans-RuCl$_2$(NBD)(py)$_2$ (1 mg, 0.33 mM), and R-bimaH (7) (0.33 mM) were placed in a pre-oven-dried (120° C.) Schlenk. Freshly distilled toluene (2.8 mL) was added, the mixture degassed by running Ar through the solution (5 min), and the mixture stirred at 100° C. for 20 min. After quickly cooling to RT, acetophenone (0.12 mL, S/C=1000) was added. The mixture was then added under Ar to a pre-oven-dried (120° C.) 100-mL glass autoclave containing solid KO-t-C$_4$H$_9$ (7.3 mg, 20 mM) and a magnetic stirring bar. H$_2$ was introduced under 4 atm pressure with several quick release-fill cycles before being set to the desired pressure. The solution was vigorously stirred at 25° C. and H$_2$ consumption monitored. Following designated reaction time, the H$_2$ was released, and a small aliquot of the crude product mixture was analyzed by chiral GC to determine conversion and ee of phenylethanol: $^1$H NMR (300 MHz, CDCl$_3$) δ 7.38-7.25 (m, aromatic protons, 5H), 4.87 (q, J=6.6 Hz, 1H), 2.03 (br, 1H), 1.48 (d, J=6.6 Hz, 3H); GC: BETA-DEX™ 120 fused silica capillary column (df=0.25 □m, 0.25 □m i.d., 30 m, Supelco); P=100.3 kPa; T=125° C.; t$_R$ of (R)-isomer=12.3 min; t$_R$ of (S)-isomer=12.9 min. The results were shown below in Table 1.

TABLE 1

Asymmetric hydrogenation of acetophenone catalyzed by in situ generated catalysts comprised of RuCl$_2$(binap)(dmf)$_n$ (26) or trans-RuCl$_2$[(R,S)-Josiphos](pyridine)$_2$ [(R,S)-27] and R-bimaH ligands (R-7).$^a$

| | Catalyst components | | | Time | Yield | ee (%)$^b$ |
|---|---|---|---|---|---|---|
| Entry | complex | ligand | Solvent | (h) | (%) | (config) |
| 1 | (S)-24 | H-7 | Toluene | 8 | 100 | 77 (S) |
| 2 | (S)-24 | H-7 | i-PrOH | 8 | 100 | 25 (S) |
| 3 | (S)-24 | (S)-Me-7 | Toluene | 8 | 100 | 91 (S) |
| 4 | (R)-24 | (R)-Me-7 | Toluene | 8 | 100 | 91 (R) |
| 5 | (S)-24 | (S)-Me-7 | i-PrOH | 8 | 100 | 28 (S) |
| 6 | (S)-24 | (S)-iPr-7 | Toluene | 12 | 100 | 87 (S) |
| 7 | (S)-24 | (S)-tBu-7 | Toluene | 10 | 100 | 91 (S) |
| 9 | (R,S)-25 | (S)-Me-7 | Toluene | 9 | 95 | 91 (S) |

$^a$Hydrogenation conditions: [ketone] = 0.33 M, [26 or 27] = 0.33 mM, [7] = 0.33 mM, P(H$_2$) = 8 atm, [KO-t-C$_4$H$_9$] = 20 mM, t = 25° C.
$^b$Enantiomeric excess (ee) determined by GC analysis; absolute configuration (config) determined from [□]$_D$ measurement.

Example 20

Additive effect in in-situ hydrogenation using R-bimaH and additive

Accurately weighed amounts of RuCl$_2$[(R,S)-Josiphos] (PPh$_3$) (1.1 mg, 0.33 mM) or trans-RuCl$_2$(NBD)(py)$_2$ (1 mg, 0.33 mM), and R-bimaH (7) (0.33 mM) were placed in a pre-oven-dried (120° C.) Schlenk. Freshly distilled toluene (2.8 mL) was added, the mixture degassed by running Ar through the solution (5 min), and the mixture stirred at 100° C. for 20 min. After quickly cooling to RT, acetophenone (0.12 mL, S/C=1000) was added. The mixture was then added under Ar to a pre-oven-dried (120° C.) 100-mL glass autoclave containing solid KO-t-C$_4$H$_9$ (7.3 mg, 20 mM), phosphine additive (e.g. 0.8 mg, 1 mM for PPh$_3$) and a magnetic stirring bar. H$_2$ was introduced under 4 atm pressure with several quick release-fill cycles before being set to the desired pressure. The solution was vigorously stirred at 25° C. and H$_2$ consumption monitored. Following designated reaction time, the H$_2$ was released, and a small aliquot of the crude product mixture was analyzed by chiral GC to determine conversion and ee of phenylethanol. The results were shown below in Table 2.

TABLE 2

Phosphine addition effect in asymmetric hydrogenation of acetophenone catalyzed by in situ generated catalysts comprised of trans-RuCl$_2$[(R,S)-Josiphos](pyridine)$_2$ [(R,S)-27] and R-bimaH ligands (R-7).$^a$

| | Catalyst components | | | | Time | Yield | ee (%)$^b$ |
|---|---|---|---|---|---|---|---|
| Entry | complex | ligand | Additive | Solvent | (h) | (%) | (config) |
| 8 | (R,S)-27 | H-7 | P(C$_6$H$_5$)$_3$ | Toluene | 9 | 100 | 82 (S) |
| 10 | (R,S)-27 | (S)-Me-7 | P(C$_6$H$_5$)$_3$ | Toluene | 9 | 100 | 96 (S) |
| 11 | (R,S)-27 | (S)-iPr-7 | P(C$_6$H$_5$)$_3$ | Toluene | 9 | 100 | 96 (S) |
| 12 | (R,S)-27 | (S)-tBu-7 | P(C$_6$H$_5$)$_3$ | Toluene | 9 | 50 | 93 (S) |

TABLE 2-continued

Phosphine addition effect in asymmetric hydrogenation of acetophenone catalyzed by in situ generated catalysts comprised of trans-RuCl$_2$[(R,S)-Josiphos](pyridine)$_2$ [(R,S)-27] and R-bimaH ligands (R-7).[a]

| Entry | Catalyst components complex | ligand | Additive | Solvent | Time (h) | Yield (%) | ee (%)[b] (config) |
|---|---|---|---|---|---|---|---|
| 13 | (R,S)-27 | (S)-Me-7 | P(C$_6$H$_5$)$_3$ | iPrOH | 9 | 100 | 78 (S) |
| 14 | (R,S)-27 | (S)-Me-7 | P(C$_6$H$_5$)$_3$ | tBuOH | 8 | 100 | 93 (S) |
| 15 | (R,S)-27 | (S)-Me-7 | P(C$_6$H$_5$)$_3$ | THF | 9 | 100 | 89 (S) |
| 16 | (R,S)-27 | (S)-Me-7 | P(C$_6$H$_5$)$_3$ | Et$_2$O | 9 | 100 | 92 (S) |
| 17 | (R,S)-27 | (S)-Me-7 | P(4-ClC$_6$H$_4$)$_3$ | Toluene | 12 | 100 | 90 (S) |
| 18 | (R,S)-27 | (S)-Me-7 | P[3,5-(C$_6$H$_5$)$_2$C$_6$H$_3$]$_3$ | Toluene | 12 | 100 | 82 (S) |
| 21 | (R,S)-27 | (S)-Me-7 | P(CH$_2$CH$_2$CH$_2$CH$_3$)$_3$ | Toluene | 18 | 52 | 98 (S) |
| 21 | (R,S)-27 | (S)-Me-7 | H$_2$O | Toluene | 18 | 100 | 96 (S) |

[a]Hydrogenation conditions: [ketone] = 0.33 M, [25] = 0.33 mM, [7] = 0.33 mM, P(H$_2$) = 8 atm, [KO-t-C$_4$H$_9$] = 20 mM, [additive] = 1.0 mM (3 equiv), t = 25° C.
[b]Enantiomeric excess (ee) determined by GC analysis; absolute configuration (config) determined from [□]$_D$ measurement.

Example 21

AH of aromatic ketones using complex (RS,S)-8 with a S/C equal to 50,000

Accurately weighed amounts of (RS,S)-8 (2.5 mg, 0.038 mM), solid KO-t-C$_4$H$_9$ (120 mg, 16.4 mM) and PPh$_3$ (60 mg, 3.4 mM) were placed in a pre-oven-dried (120° C.) 350-mL autoclave containing a magnetic stirring bar, and placed under high vacuum for at least 20 min before purging with argon. Freshly distilled solvent (toluene, 35 mL; t-BuOH, 15 mL) and purified acetophenone (15 mL, 1.9 M, S/C=50,000) were placed into a pre-dried Schlenk and degassed by 3 cycles of freeze-and-thaw and then added to the autoclave under an Ar atmosphere. H$_2$ was introduced under 20 atm pressure with several quick release-fill cycles before being set to 40 atm. The solution was vigorously stirred at 25° C. and H$_2$ consumption monitored. The H$_2$ was carefully released after 10 h, the solution passed through a short pad of silica gel and solvent removed under reduced pressure. The crude product mixture was analyzed by chiral GC to determine conversion and ee of (S)-phenylethanol. GC: BETA-DEX™ 120 fused silica capillary column (df=0.25 m, 0.25 mm i.d., 30 m, Supelco); P=100.3 kPa; T=125° C.; t$_R$ of (R)-7a=12.3 min; t$_R$ of (S)-7a=12.9 min(major). Conv.>99%; ee=97%.

Example 22

AH of aromatic ketones using complex (RS,S)-8

Several aromatic ketones were reduced using the same process described in Example 19. The hydrogenation conditions and results were shown in Table 3.

TABLE 3

Asymmetric hydrogenation of simple aryl ketones catalyzed by RuCl$_2$[(R,S)-Josiphos)][(S)-Me-bimaH)][(RS,S)-8] complex.[a]

| Entry | Substrate | S/C ratio | P/H$_2$ (atm) | Time (h) | Yield (%)[b] | ee (%)[b] (config)[c] |
|---|---|---|---|---|---|---|
| 1 | acetophenone | 1,000 | 8 | 2 | 100 | 96 (S) |
| 2 | acetophenone | 10,000 | 20 | 12 | 100 | 96 (S) |
| 3[d] | acetophenone | 50,000 | 40 | 10 | 100 | 97 (S) |
| 4 | 4-MeO-acetophenone | 5,000 | 20 | 16 | 95 | 97 (S) |
| 5 | 4-CF$_3$-acetophenone | 5,000 | 20 | 8 | 90 | 82 (S) |
| 6 | 2-Me-acetophenone | 5,000 | 20 | 8 | 100 | 95 (S) |
| 7 | 3-Br-acetophenone | 5,000 | 20 | 6 | 100 | 92 (S) |
| 8[e] | 2-chlorobenzophenone | 5,000 | 20 | 24 | 95 | 99 (R) |
| 9 | 2-acetylthiophene | 1,000 | 8 | 12 | 92 | 94 (S) |

TABLE 3-continued

Asymmetric hydrogenation of simple aryl ketones catalyzed by RuCl$_2$[(R,S)-Josiphos)][(S)-Me-bimaH)][(RS,S)-8] complex.[a]

| Entry | Substrate | S/C ratio | P/H$_2$ (atm) | Time (h) | Yield (%)[b] | ee (%)[b] (config)[c] |
|---|---|---|---|---|---|---|
| 10 | (1-phenylpropan-1-one) | 1,000 | 8 | 12 | 100 | 97 (S) |

[a]Hydrogenation conditions: [ketone] = 0.3-1.9M, [(RS,S)-8] = 0.04-0.3 mM, [KO-t-C$_4$H$_9$] = 15-20 mM, [PPh$_3$] = 1.0-3.4 mM, t = 25° C., solvent = toluene/t-BuOH (9/1).
[b]Determined by GC.
[c]Absolute configuration (config) determined from [□]$_D$.
[d]Toluene/t-BuOH (7/3).
[e]Yield determined by $^1$H NMR; ee determined by HPLC.

Example 23

Screening of diphosphane ligands in asymmetric hydrogenation of acetophenone

The acetophenone reduction results using different phosphines and (S)-Me-bimaH are given in Table 4. The hydrogenation procedure was the same as described in Example 19. The H$_2$ pressure is always 8 atm.

TABLE 4

AH of acetophenone using different chiral diphosphanes and (S)-Me-bimaH within a 1 h hydrogenation period.[a]

| Entry | Bis-P Ligand | S/C | Conv. % | Ee % (S) |
|---|---|---|---|---|
| 1 | (S)-PhanePHOS | 1000 | 100 | 78 |
| 2 | (S)-SEGPHOS | 1000 | 100 | 89 |
| 3 | (S,S)-DIOP | 1000 | 100 | 96 |
| 4 | (S)-Cl—MeO-BIPHEP | 1000 | 100 | 86 |
| 5 | (S,S)-DIPAMP | 1000 | NR | \ |
| 6 | (S)-BINAP | 1000 | 90 | 88 |
| 7 | (S,S)-DuPHOS | 1000 | 1 | 0 |
| 8 | (S,S)-WalPHOS | 1000 | 62 | 13 |
| 9 | (R,S)-Josiphos | 1000 | 13 | 71 |

[a]Conditions: Substrate/Catalyst/Base ratio = 1000/1/50; V$_T$ = 3 ml; t = 1 h; 25° C.

Example 24

AH of aromatic ketones using complex (SS,S)-9

Accurately weighed amounts of (SS,S)-9 (0.9 mg, 1 mop, solid KO-t-C$_4$H$_9$ (6 mg, 0.05 mmol) and sometimes derivatives [eg. PPh$_3$ (0.3 mg, 1 µmol)] were placed in a pre-oven-dried (120° C.) 350-mL autoclave containing a magnetic stirring bar, and placed under high vacuum for at least 20 min before purging with argon. Freshly distilled solvent (toluene, 2.7 mL; t-BuOH, 0.3 mL) and purified ketones (1 mmol, S/C=1,000) were placed into a pre-dried Schlenk and degassed by 3 cycles of freeze-and-thaw and then added to the autoclave under an Ar atmosphere. H$_2$ was introduced under 20 atm pressure with several quick release-fill cycles before being set to 8 atm. The solution was vigorously stirred at 25° C. and H$_2$ consumption monitored. The H$_2$ was carefully released after a period of time, the solution passed through a short pad of silica gel and solvent removed under reduced pressure. The crude product mixture was analyzed by $^1$H NMR to determine conversion and chiral GC or HPLC to determine ee of the chiral alcohol products. The hydrogenation results are given in Table 5.

TABLE 5

Screening of aromatic substrates using complex (SS,S)-9[a]

| Entry | sub | PPh$_3$[b] | t/h | Conv. % | Ee % (S) |
|---|---|---|---|---|---|
| 1 | acetophenone | \ | 1 | 100 | 96 |
| 2 | acetophenone | 3 eq | 1 | 62 | 98 |
| 3 | acetophenone | 1 eq | 1 | 100 | 98 |
| 4 | 2-Me-acetophenone | \ | 13.5 | 87 | 90 |
| 5 | 2-Me-acetophenone | 1 eq | 8.5 | 74 | 97 |
| 6 | 4-MeO-acetophenone | \ | 5 | 99 | 97 |
| 7 | 4-MeO-acetophenone | 1 eq | 3 | 99 | 99.6 |
| 8 | 4-Br-acetophenone | \ | 15 | 100 | 93 |
| 9 | 4-Br-acetophenone | 1 eq | 6 | 99 | 98 |
| 10 | 4-F-acetophenone | 1 eq | 9.5 | 100 | 98 |
| 11 | 4-Me-acetophenone | 1 eq | 12 | 99 | 98 |
| 12 | 3-Br-acetophenone | 1 eq | 1.5 | 99 | 98 |
| 13 | 3,5-CF$_3$-acetophenone | 1 eq | 3 | 100 | 92 |
| 14 | (1-phenylpropan-1-one) | 1 eq | 5 | 100 | 99 |
| 15 | (1-(naphthalen-2-yl)ethan-1-one) | 1 eq | 2 | 99 | 99 |
| 16 | (1-(4-aminophenyl)ethan-1-one) | 1 eq | 10 | 90 | 98 |
| 17 | (ethyl 4-acetylbenzoate) | 1 eq | 3 | 97 | 91 |

TABLE 5-continued

Screening of aromatic substrates using complex (SS,S)-9[a]

| Entry | sub | PPh$_3$[b] | t/h | Conv. % | Ee % (S) |
|---|---|---|---|---|---|
| 18[c] |  | 1 eq | 8 | 99 | 99 |

[a]Conditions: Substrate/Catalyst/Base = 1000/1/50; V$_T$ = 3 mL, 25-30° C.
[b]Compared to catalyst;
[c]The H$_2$ pressure was 20 atm and the configuration of the product was R.

Example 25

Asymmetric hydrogenation of dialkyl ketone using (S,S)-18

Accurately weighed amounts of (S,S)-18 (2.9 mg, 3.0 μmol), solid KO-t-C$_4$H$_9$ (6 mg, 0.05 mmol) were placed in a pre-oven-dried (120° C.) 350-mL autoclave containing a magnetic stirring bar, and placed under high vacuum for at least 20 min before purging with argon. Freshly distilled solvent (2-PrOH, 3 mL) and purified pinacolone (0.62 g, 6.0 mmol, S/C=2,000) were placed into a pre-dried Schlenk and degassed by 3 cycles of freeze-and-thaw and then added to the autoclave under an Ar atmosphere. H$_2$ was introduced under 20 atm pressure with several quick release-fill cycles before being set to 8 atm. The solution was vigorously stirred at 25° C. and H$_2$ consumption monitored. The H$_2$ was carefully released after a period of time (12 h), the solution passed through a short pad of silica gel and solvent carefully removed under reduced pressure. The crude product mixture was analyzed by chiral GC: CP-Chirasil-DEX CB column, P=41 kPa, T(column)=60° C., T(injection)=200° C., T(detector)=200° C., t$_R$ of (R)-isomer=17.2 min, t$_R$ of (S)-isomer=17.9 min. Conv., 100%; ee, 75%.

C. Catalytic Tests in Asymmetric Transfer Hydrogenation

Example 26

Asymmetric transfer hydrogenation of acetophenone using (RS,S)-8

Accurately weighed amounts of (RS,S)-8 (1.0 mg, 1 μmol) and solid KO-t-C$_4$H$_9$ (4.5 mg, 0.04 mmol) were placed in a pre-oven-dried (120° C.) 30-mL Schlenk tube containing a magnetic stirring bar, and placed under high vacuum for at least 20 min before purging with argon. Freshly distilled solvent (i-PrOH, 3 mL) and purified acetophenone (0.12 mL, 1 mmol, S/C=1,000) were placed into a pre-dried Schlenk and degassed by bubbling for 5 min and then added to the Schlenk tube above under an Ar atmosphere. The solution was vigorously stirred at 80° C. for 12 h, then the solution was passed through a short pad of silica gel and solvent removed under reduced pressure. The crude product mixture was analyzed by chiral GC to determine conversion and ee of (S)-phenylethanol. GC: BETA-DEX™ 120 fused silica capillary column (df=0.25 m, 0.25 mm i.d., 30 m, Supelco); P=100.3 kPa; T=125° C.; t$_R$ of (R)-isomer=12.3 min; t$_R$ of (S)-isomer=12.9 min(major). Conv.=95%; ee=15%.

D. Asymmetric Hydrogenation Reaction Profile Using (RS,S)-8

Hydrogenations were conducted in a glass autoclave equipped with a sampling needle connected to a three-way stop valve. An accurately measured mass of (RS,S)-8, KO-t-C$_4$H$_9$ and (where applicable) PPh$_3$ were placed into a pre-dried (120° C.) glass autoclave containing a magnetic stirring bar, which was then maintained under high vacuum for at least 5 min prior to purging with argon. Into a pre-dried Schlenk tube were placed accurately measured amounts of acetophenone and a solvent such that the desired [(RS,S)-8], [acetophenone], S/C ratio, [PPh$_3$] and [KO-t-C$_4$H$_9$] were obtained. The reaction mixture was degassed by three freeze-thaw cycles and added under Ar to the autoclave. If needed, the autoclave was placed in a pre-warmed oil-bath set at the desired reaction temperature. H$_2$ was introduced under 4 atm pressure with several quick release-fill cycles before being set to the desired pressure. Stirring and timing (t=0 min) were immediately commenced. Reaction samples were obtained (2 drops into an ether-filled GC sample tube) at specified time-intervals (t), and the extent of substrate consumption and ee of phenylethanol determined by GC.

Example 27

Effects of added PPh$_3$ for toluene systems

Figure 1:
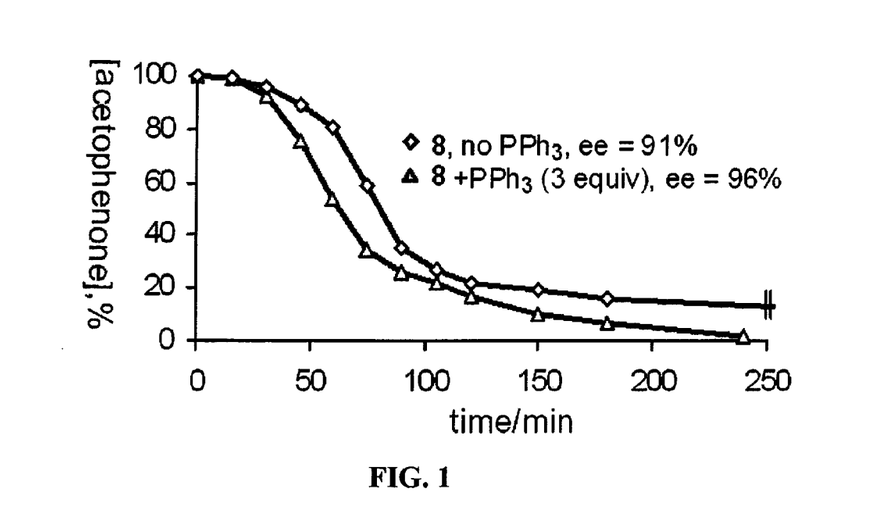
FIG. 1 is a chart that shows the effect of PPh$_3$ on hydrogentation in toluene solvent.

Conditions: [(RS,S)-8]=0.33 mM; [acetophenone]=0.33 M; P(H$_2$)=4 atm; [KO-t-C$_4$H$_9$]=15 mM; [PPh$_3$]=0 or 1 mM; S/C=1000; T=25° C.; V$_T$=3 mL, solvent=toluene. The results are shown graphically in FIG. 1.

Example 28

Hydrogenation in t-BuOH solvent

Figure 2:
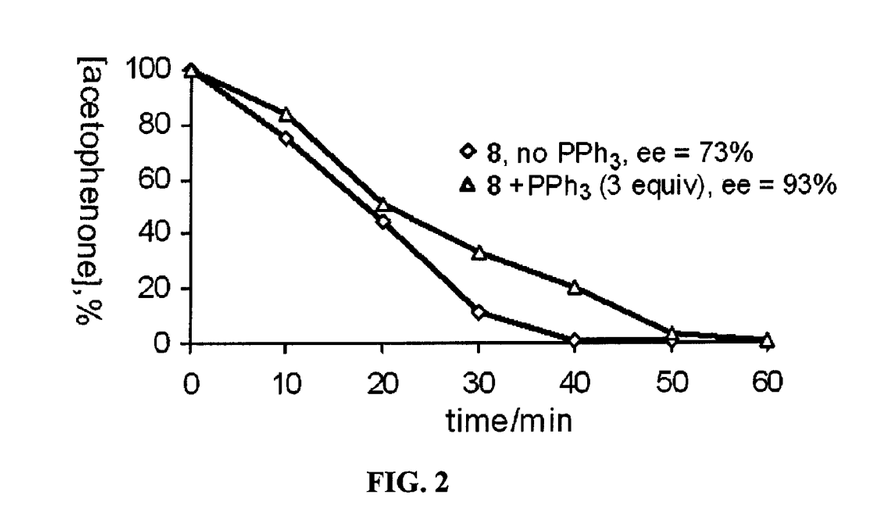
FIG. 2 is a chart that shows the effect of PPh$_3$ on hydrogentation in t-BuOH solvent.

Conditions: [(RS,S)-8]=0.33 mM; [acetophenone]=0.33 M; P(H$_2$)=4 atm; [KO-t-C$_4$H$_9$]=15 mM; [PPh$_3$]=0 or 1 mM; S/C=1000; T=30° C.; V$_T$=3 mL, solvent=(CH$_3$)$_3$COH. The results are shown graphically in FIG. 2.

Extra statements about the Hydrogenation reactions above:
The solvents used can be at least one of those shown below: benzene, toluene, xylene, methylxylene, THF, CH$_2$Cl$_2$, Et$_2$O, CH$_3$OH, EtOH, iPrOH, nPrOH, nBuOH, iBuOH, tBuOH, MeCN, ethylene glycol dimethyl ether, CHCl$_3$, DMSO, DMF etc.
The base used can be tBuOK, tBuONa, tBuOLi, tBuOCs, NaOH, KOH, Cs$_2$CO$_3$, Na$_2$CO$_3$, K$_2$CO$_3$, NaHCO$_3$, KHCO$_3$, K$_3$PO$_4$, K$_2$HPO$_3$, KH$_2$PO$_3$, KF, NaH, KH, CaH$_2$, Et$_3$N, TMEDA, DABCO, DBU, pyridine etc.
The reaction is tolerant to small amount of water.
The reaction is tolerant to substrates with functional groups: eg. ester [—C(=O)O—], amine (NH$_2$).
The substrates can be heteroaromatic ketones.
The reaction time can be 0.1-48 hours, the H$_2$ pressure can be 1-80 atm.

The invention claimed is:
1. A novel class of ruthenium complexes having general formula (I) represented as [RuLmL'XY], in which
X is Cl, Br, I or hydrogen, Y is Cl, Br, I, hydrogen or BH$_4$;
L is ligand selected from the following groups:
a) monophosphine having general formula R$^1$R$^2$R$^3$P, wherein R$^1$, R$^2$, R$^3$ is aliphatic alkyl groups or aromatic groups having 1 to 10 carbon atoms;
b) bidentate phosphine with general formula R$^5$R$^6$P—R$^4$—PR$^7$R$^8$, wherein R$^4$ is a chiral or achiral organic hydrocarbon backbone; $R^5$, $R^6$, $R^7$ and $R^8$ is aliphatic alkyl group or aromatic groups having 1 to 10 carbons;

m is 2 when equal monodentate phosphine ligands are selected from group a); m is 1 when the bisphosphine is selected from b);

L' is a bidentate hybrid amine ligand selected from the following groups (structure II to structure V):

II

III

IV

V wherein $R^9$ is hydrogen or alkyl groups having 1 to 8 carbon atoms, when $R^9$ is not hydrogen, the aforementioned hybrid amine ligands (II to V) are chiral ligands having either R or S configuration; the alkyl group for $R^9$ is selected from a group consisting of methyl, ethyl, propyl, isopropyl, butyl, isobutyl, tertiary-butyl, isopentyl, cyclopentyl, isohexyl, cyclohexyl, phenyl and benzyl;

$R^{10}$, $R^{11}$, $R^{12}$ are independently hydrogen or alkyl groups, aryl groups, arylalkyl groups, each having up to 12 carbon atoms; the alkyl groups are selected from a group consisting of methyl, ethyl, propyl, butyl, isobutyl, tertiary-butyl, pentyl, hexyl, isopentyl, cyclopentyl and cyclohexyl; the aryl groups are phenyl or substituted phenyls, the arylalkyl group are benzyl or alkyl-substituted benzyl;

A is alkyl, alkoxy or aryl group, each having 1 to 8 carbon atoms; A is also independently hydrogen, halogen, nitro, amino, sulfonic acid; n is an integer from 1 to 6 equal to the number of unsubstituted aromatic ring carbons; the alkyl group for A is selected from a group consisting of methyl, ethyl, propyl, isopropyl, butyl, isobutyl, tertiary-butyl, isopentyl, cyclopentyl, cyclohexyl, fluoromethyl and trifluoromethyl; alkoxy group for A is methoxy, ethoxy or tertiary-butoxy; aryl group for A is phenyl, substituted phenyl, benzyl or substituted benzyl.

2. The ruthenium complexes as claimed in claim 1, wherein in the formula (VI) [RuL$_2$L'XY], L is a monophosphine ligand selected from group a); L' is bidentate hybrid amine ligands selected from the groups being represented by structure II, III, IV and V; X is halogen or hydrogen, Y is halogen, hydrogen or BH$_4$; X and Y ligands are trans or cis in the ruthenium complexes.

3. The ruthenium complexes as claimed in claim 1, wherein in the formula VII: [RuL$_1$L'XY], L is bidentate phosphine ligands selected from group b), the bidentate phosphine ligand is chiral or achiral, the chiral bidentate phosphine ligand is selected from the following ligands: BINAP and its analogue bisphosphine with chiral binaphthyl or substituted binaphthyl backbones, BIPHEP and its analogue bisphosphine with chiral biphenyl backbone, JOSIPHOS and analogue bisphosphine with a ferrocene or substituted ferrocene backbone, DIOP, NORPHOS, SKEWPHOS, CHIRAPHOS, PHANEPHOS;

L' is the bidentate hybrid amine ligands being represented by structure II, III, IV and V;

X is halogen or hydrogen; Y is halogen, hydrogen or BH$_4$; X and Y ligands are trans or cis in the ruthenium complexes.

4. A preparation method for the ruthenium complexes as claimed in claim 1, wherein the ruthenium complexes are prepared from ruthenium compounds, hybrid bidentate amine ligands, bidentate phosphines or monodentate phosphines ligands in organic solvents at 20~120° C. for 0.5~20 hours, the molar ratio of the ruthenium compounds, amine ligands, bisphosphine or monophosphine ligands is 1:1~3:1~5.

5. The preparation method as claimed in claim 4, wherein for the complexes, the ruthenium metal compounds are halogenide of Ru complexes or their derivatives, such as [RuX$_2$(C$_6$H$_6$)]$_2$, RuCl$_2$(PPh$_3$)$_3$, RuX$_3$, wherein X is Cl, Br, or I.

6. The preparation method as claimed in claim 4, wherein for the complexes, when monophosphine ligands are employed, the molar ratio of transition metal compound, bidentate amine and monophosphine is 1:1~3:1~5.

7. The preparation method as claimed in claim 4, wherein for the complexes, when bidentate phosphine ligands are employed, the molar ratio of transition metal compound, bidentate amine and bidentate phosphine ligands is 1:1~3:1~3.

8. The ruthenium complexes as claimed in claim 1, wherein the complexes of the general formula (I) are represented as [RuL1L'XY], in which X is Cl, Br, I or hydrogen, Y is Cl, Br, I, hydrogen or BH$_4$; L is DIOP;

III wherein $R^9$ is hydrogen or alkyl groups having 1 to 8 carbon atoms, when $R^9$ is not hydrogen, the bidentate hybrid amine ligand having structure III is a chiral ligand having either R or S configuration; the alkyl group for $R^9$ is selected from the group consisting of methyl, ethyl, propyl, isopropyl, butyl, isobutyl, tertiary-butyl, isopentyl, cyclopentyl, isohexyl, cyclohexyl, phenyl and benzyl;

A is alkyl, alkoxy or aryl group, each having 1 to 8 carbon atoms; A is also independently hydrogen, halogen, nitro, amino, sulfonic acid; n is an integer from 1 to 6 equal to the number of unsubstituted aromatic ring carbons; the alkyl group for A is selected from a group consisting of methyl, ethyl, propyl, isopropyl, butyl, isobutyl, tertiary-butyl, isopentyl, cyclopentyl, cyclohexyl, fluoromethyl and trifluoromethyl; alkoxy group for A is methoxy, ethoxy or tertiary-butoxy; aryl group for A is phenyl, substituted phenyl, benzyl or substituted benzyl.

9. A preparation method for the ruthenium complexes as claimed in claim 8, wherein the ruthenium complexes are prepared from ruthenium compounds, hybrid bidentate amine ligands, DIPO in organic solvents at 20~120° C. for 0.5~20 hours, the molar ratio of the ruthenium compounds, amine ligands, DIPO is 1:1~3:1~5.

10. The preparation method as claimed in claim 9, wherein for the complexes, the ruthenium metal compounds are halogenide of Ru complexes or their derivatives, such as [RuX$_2$(C$_6$H$_6$)]$_2$, RuCl$_2$(PPh$_3$)$_3$, RuX$_3$, wherein X is Cl, Br, or I.

11. The preparation method as claimed in claim 10, wherein the molar ratio of transition metal compound, bidentate amine and DIPO is 1:1~3:1~3.

12. A method of catalytic hydrogenation of simple ketones comprising the steps of providing the Ru complexes as claimed in claim 8, and catalytically hydrogenating simple ketones with said Ru complexes, the ketones having aryl or unsaturated alkyl group on α-position, ketones having bulky alkyl group on α-position, diaryl ketones and its derivatives, ketones having heteroaromatic group on α-position, β-N,N-dimethylamino-α-phenyl ketone and its derivatives.

13. Method of claim 12, wherein in the catalytic hydrogenation of simple ketones comprises catalytically hydrogenating simple ketones to secondary alcohols, wherein the catalytic reactivity and enantioselectivity of the said Ru complexes is further enhanced by the addition of some additives in the asymmetric hydrogenation of simple ketones.

14. Method of claim 13, wherein the additives are monodentate tertiary phosphines or monodentate tertiary amines selected from the group consisting of triphenylphosphine, tri(4-methyphenyl)phosphine, tri(4-methoxyphenyl)phosphine, tri(3,5-dimethylphenyl)phosphine, and triethylamine, and wherein the molar ratio of the additives to the ruthenium metal is 3~1:1.

15. Method of claim 12, wherein reduction of simple ketones is performed in either protonic or aprotonic solvents, or the mixture of protonic and aprotonic solvents; the protonic solvents are selected from the group consisting of methanol, ethanol, propanol, isopropanol, butanol, isobutanol and tertiary-butanol; and the aprotonic solvents are selected from the group consisting of toluene, tetrahydrofuran, acetonitrile, dichloromethane, dimethylformamide, diethyl ether, dimethylsulfonamide and N-methylpyrrolidinone.

* * * * *